United States Patent
Forno et al.

[19]

[11] Patent Number: 5,851,484
[45] Date of Patent: Dec. 22, 1998

[54] SAFETY SYSTEM FOR CONTAMINATED INSTRUMENTS

[76] Inventors: JoAnn Forno, Box 53, Addison, Pa. 15411; Linda Lohr, 1525 Hyndman St., South Connellsville, Pa. 15425

[21] Appl. No.: 590,491

[22] Filed: Jan. 24, 1996

[51] Int. Cl.[6] .................................................. A61L 2/00
[52] U.S. Cl. ..................... 422/28; 422/32; 422/292; 422/300; 206/363; 206/370; 206/564
[58] Field of Search ........................... 422/292, 300, 422/28, 32; 206/363, 370, 564; 220/83

[56] References Cited

U.S. PATENT DOCUMENTS

| | | | |
|---|---|---|---|
| 3,768,971 | 10/1973 | Fishpaw | 422/300 |
| 4,174,816 | 11/1979 | Olson | 242/475 |
| 4,643,303 | 2/1987 | Arp et al. | 422/300 X |
| 4,732,187 | 3/1988 | Mönch | 422/300 X |
| 4,889,231 | 12/1989 | Foote et al. | 206/363 |
| 4,925,047 | 5/1990 | Valentine et al. | |
| 5,072,832 | 12/1991 | Valentine et al. | 206/570 |
| 5,080,874 | 1/1992 | Nichols | 422/300 |
| 5,381,896 | 1/1995 | Simons | 206/370 |
| 5,415,180 | 5/1995 | Horan | 128/846 |
| 5,511,674 | 4/1996 | Boyd et al. | 211/70.6 |

OTHER PUBLICATIONS

"Safe–T–Strainer" & Flexi–Basin Brochure from Devon Industries, Inc., product catalog, Sep. 1, 1995.
2 photographs of soaking tray; Soaking trays with inner strainers are used to soak contaminated instruments prior to cleaning. No Date Available.

*Primary Examiner*—Krisanne Thornton
*Attorney, Agent, or Firm*—Oldham & Oldham Co., L.P.A.

[57] ABSTRACT

A system and method for handling contaminated operating room surgical instruments includes a rectangular porous strainer which is sufficiently large to fully contain a variety of surgical tools and instruments and a waterproof rectangular basin, sized to receive the strainer. The basin is adapted to fit stably onto a conventional surgical ring stand either alone, or with a separate adapter. The system replaces conventional round surgical basins which are not capable of safely containing the larger or longer surgical instruments typical of many modern surgical procedures. Utilizing the system eliminates the current practice of manually transferring contaminated instruments from the round surgical basins into larger soaking trays for transportation to the decontamination area.

14 Claims, 7 Drawing Sheets

SAFETY SYSTEM FOR CONTAMINATED INSTRUMENTS

FIELD OF THE INVENTION

This invention relates to the field of operating room surgical instruments and devices for handling such instruments during and after surgical procedures.

BACKGROUND OF THE INVENTION

There are a wide variety of surgical tools and instruments which are used in modern surgical procedures. Many specialized surgical procedures that are now routinely performed, including less invasive laproscopic/endoscopic surgery, involve instruments that are longer or larger and more cumbersome to handle than instruments used in the past. An example of these would be laproscopic cutting, grasping and stapling instruments, etc. and certain orthopedic and abdominal surgical instruments, to name a few.

During surgical procedures, once instruments are used, operating room nurses typically place them into round surgical basins filled with a sterile solution. These basins sit into the ring portion of conventional surgical ring stands. The instruments remain in these basins on the ring stands until after the surgical procedure is concluded when the instruments are then transported to a separate decontamination area and sterilized.

With many surgical procedures, the used instruments do not fit completely into the round surgical basins because either the instruments are too long to fit into the basins or the basins simply cannot accommodate the number of instruments that have been used. In such cases, the instruments may not be safely kept in the basins. Presently, there are several types of larger soaking trays, some including an inner strainer, which are used to transport contaminated surgical instruments from an operating room to a decontamination area.

Utilizing any of these soaking trays requires the transfer, by hand, of the contaminated instruments from the round surgical basins into a soaking tray filled with enzyme pre-soak and decontamination solution and then the later transfer, by hand, of the same instruments from the soaking tray into, for example, a sink in a decontamination area. Because of this extra handling of the instruments, the current practice is inefficient and increases the likelihood of both injuries to hospital personnel and damage to the instruments.

In addition, it is also a typical practice for the soaking tray to be lifted from its transport cart onto, for example, a counter in the decontamination area. This requires the lifting of an often very heavy tray containing solution and contaminated surgical instruments. Once the instruments have been removed from the soaking tray, the solution remaining in the tray is then typically poured into a sink which requires still further lifting and tilting of the tray and creates the risk of splashing contaminated solution. Such lifting and splashing also increases the likelihood of workplace injuries.

Accordingly, there is a need for a system of handling operating room surgical instruments which can easily accommodate the larger instruments typical of today's modern surgical procedures and at the same time provide a more efficient and safer way of handling such instruments.

SUMMARY OF THE INVENTION

To these ends, in a system and method for handling operating room surgical tools and instruments, whereby both safety and efficiency in handling are improved, a rectangular porous strainer is preferably provided which is sufficiently large to fully contain a quantity of contaminated operating room surgical instruments of various shapes and sizes. A waterproof rectangular basin is advantageously sized and shaped to receive the porous strainer. The basin is adapted to fit onto a conventional surgical ring stand, either alone or with the use of an adapter.

In use, sterile surgical items, such as sponges, needle counters and instruments, can be delivered to an operating room in the sterile basin and strainer.

The basin with the strainer inside is advantageously adapted to fit onto or into a conventional surgical ring stand, in place of a traditional round basin.

When the surgical procedure is completed, the basin with the inner strainer containing contaminated instruments and enzyme pre-soak and decontamination solution is preferably covered and taken to a decontamination area, thereby eliminating the necessity of manually transferring the instruments into a separate soaking tray. The strainer provides a safer and easier way of removing the instruments from the contaminated solution. Furthermore, a drains is advantageously provided on the rectangular basin to permit hospital personnel to quickly drain the contaminated solution from the basin without having to lift the basin to pour out the liquid. The surgical ring stand is preferably used to transport the basin and strainer containing the instruments and solution. Thus handling of the surgical instruments is reduced. Furthermore, lifting of heavy trays or basins filled with contaminated surgical instruments and solution is also most desirably avoided.

BRIEF DESCRIPTION OF THE DRAWINGS

In the drawings wherein similar reference characters denote similar elements throughout the several views:

FIG. 12 is an exploded perspective view of another embodiment which includes a basin stand capable of stably

3 holding a rectangular basin without bottom supports and without using an adapter.

DETAILED DESCRIPTION OF THE INVENTION

Figure 1:
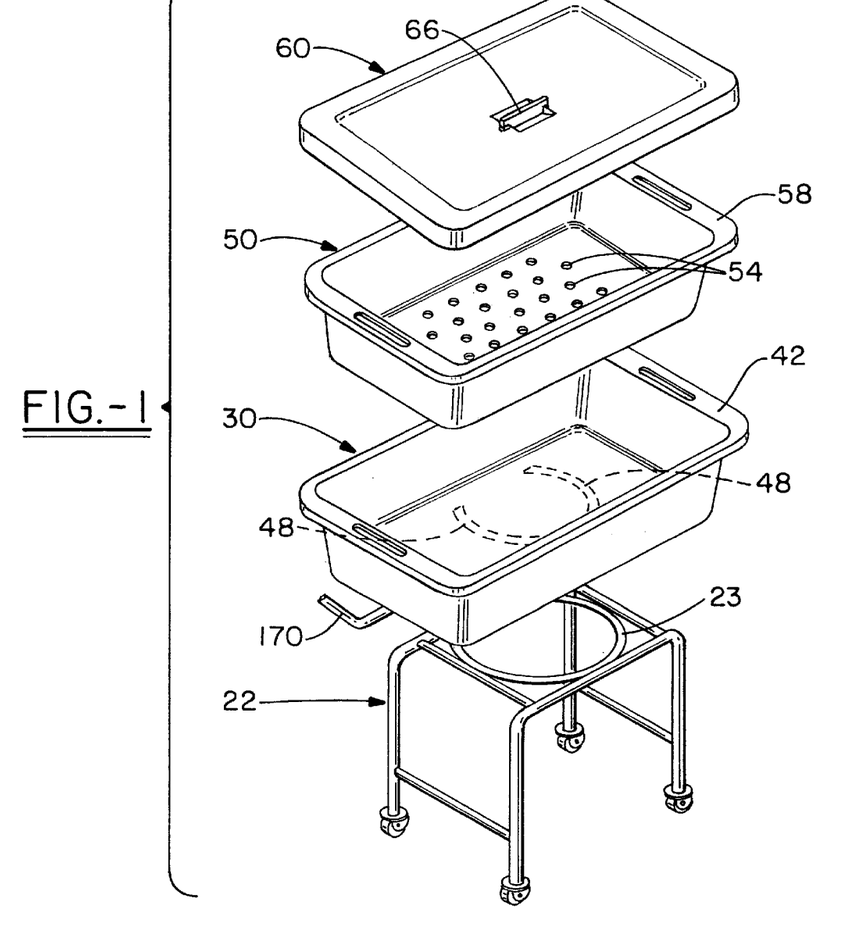
FIG. 1 is an exploded perspective view of a preferred embodiment of the present invention which includes a rectangular porous strainer which fits into a waterproof rectangular basin, and a cover which can be used when the system is being transported. In the embodiment shown, the basin is adapted to fit stably onto a conventional surgical ring stand without the need for a separate adapter.

Turning in detail to the drawings, FIG. 1 shows a preferred embodiment of the invention comprising a rigid rectangular porous strainer 50, which fits within a rectangular waterproof basin 30, and a cover 60 which fits onto the assembled basin 30 and strainer 50. The basin 30 in this embodiment includes integral bottom supports 48 which, as will be discussed in more detail below, enable the basin 30 to stably fit onto a ring 23 on a conventional surgical ring stand 22. Furthermore, the basin 30 shown in FIG. 1 has an integral rim 42 which provides additional strength and rigidity as well as a convenient feature of lifting the basin 30.

Figure 2:
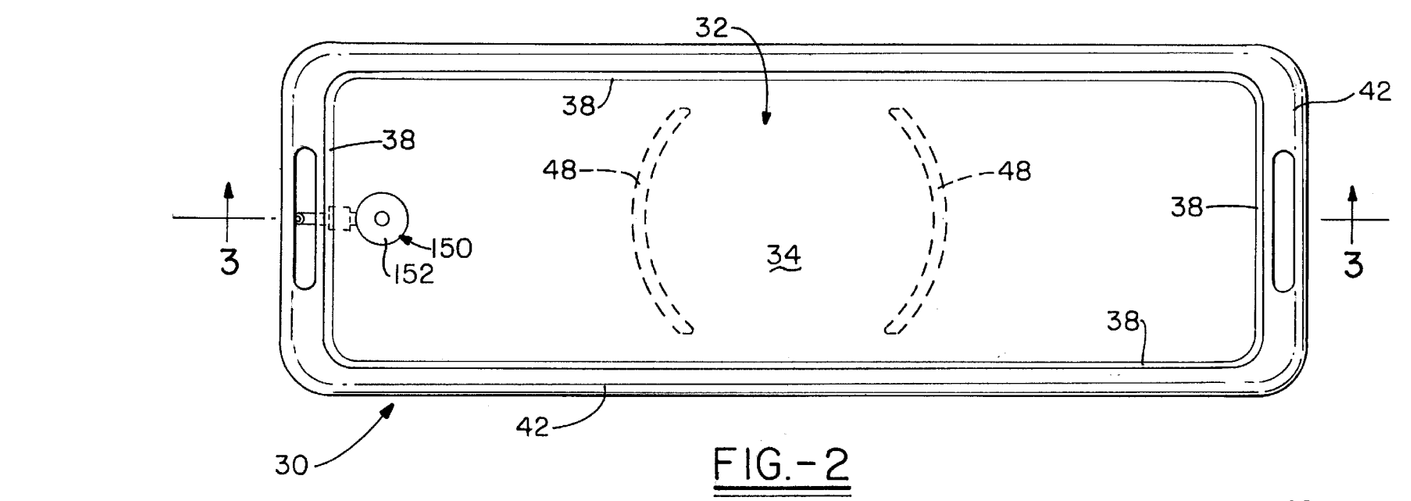
FIG. 2 is a plan view of a rectangular basin in an embodiment which includes a rim and an internal drain fitting and further includes bottom supports by which the basin fits stably onto a conventional surgical ring stand.
Figure 3:
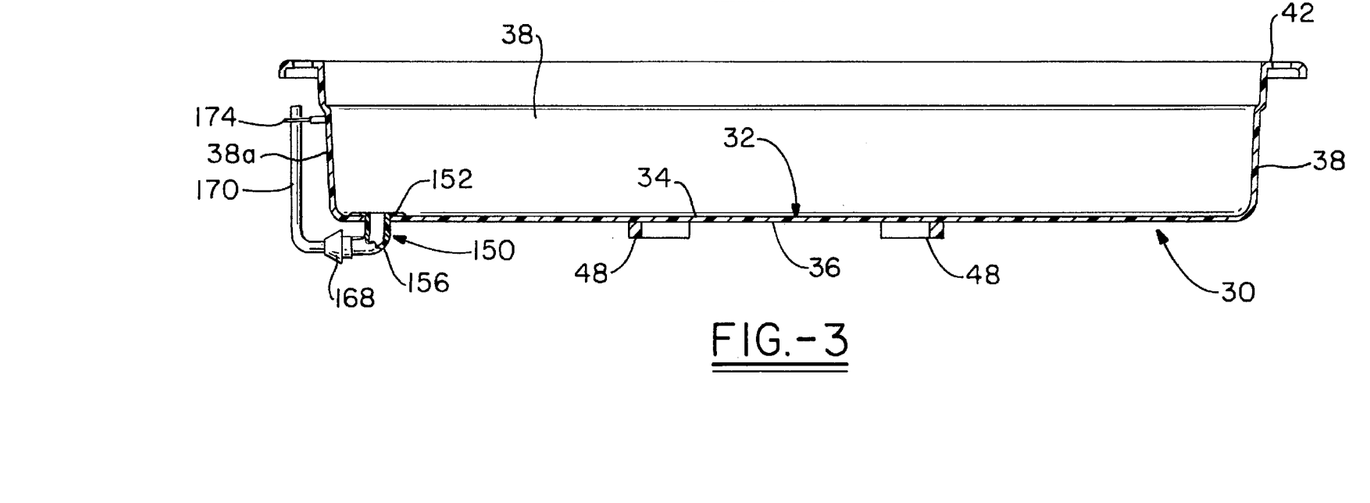
FIG. 3 is a section view of the basin of FIG. 2 taken along line 3—3.
Figure 4:
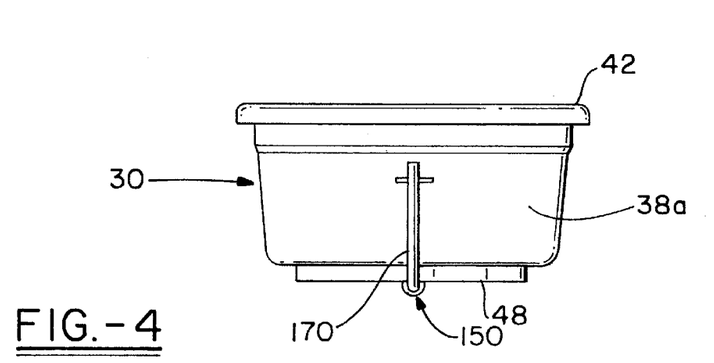
FIG. 4 is an end view of the basin of FIG. 2.

The basin 30 is shown in greater detail in FIGS. 2–4. The basin 30 has a rectangularly shaped floor 32, having a top surface 34 and a bottom surface 36 and four integral side walls 38 extending upwardly from the floor 32 and substantially perpendicular to the floor 32. The floor 32 and sidewalls 38 together form the waterproof rectangular basin 30.

Figures 14, 15:
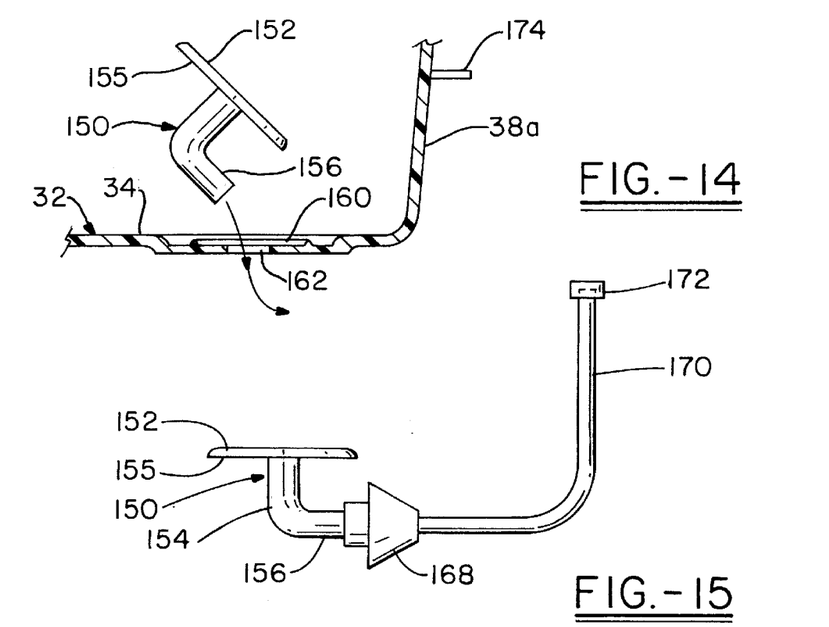
FIG. 14 is an exploded view depicting the internal drain fitting and basin of FIG. 3.
FIG. 15 is a section view of the internal drain fitting of FIG. 14.

The basin 30 also includes an internal drain fitting 150 on the floor 32 at a position near a shorter sidewall 38a. The drain fitting 150 allows solution within the basin 30 to be easily drained. It is preferred that the geometry and position of the drain fitting 150 be such that the presence of the porous strainer 50 fitted within the basin 30 would not interfere with the draining function. The drain fitting 150 is sized to permit the attachment of a length of tube 170 such as surgical tubing to aid in draining. An adapter 168 can be used to facilitate the connection of the tube 170 to the fitting 150. As seen in FIG. 15, a removable cap 172 is provided for the tube 170 to prevent accidental drainage. A hook 174 is located on sidewall 38a to securely hold the tube 170 in an upright position to prevent accidental drainage.

FIG. 15 shows the internal drain fitting of FIG. 3 in greater detail. The fitting 150 has a generally circular flange 152 having a, bottom surface 155. Extending downwardly from the flange 152 is a neck 154 with an internal bore 158. A short tubular drain spout 156 extends substantially perpendicular to the neck 154 and in fluid connection with the internal bore 158.

FIG. 14 illustrates the installation of the internal drain fitting 150 of FIGS. 3 and 15. A generally circular recess 160 corresponding in size to the flange 152 on the fitting 150 is located on the top surface 34 of the floor 32 of the basin 30. A circular opening 162 through the floor 32 is located in the center of the recess 160. The opening 162 is sufficiently large so that the drain spout 156 and neck 154 of the drain fitting 150 can pass through the opening 162. The drain fitting 150 is attached to the basin floor 32 by a sealing mechanism such as an ultrasonic seal or a glue between the recess 160 and the bottom surface 155 of the flange 152.

4

Figure 16:
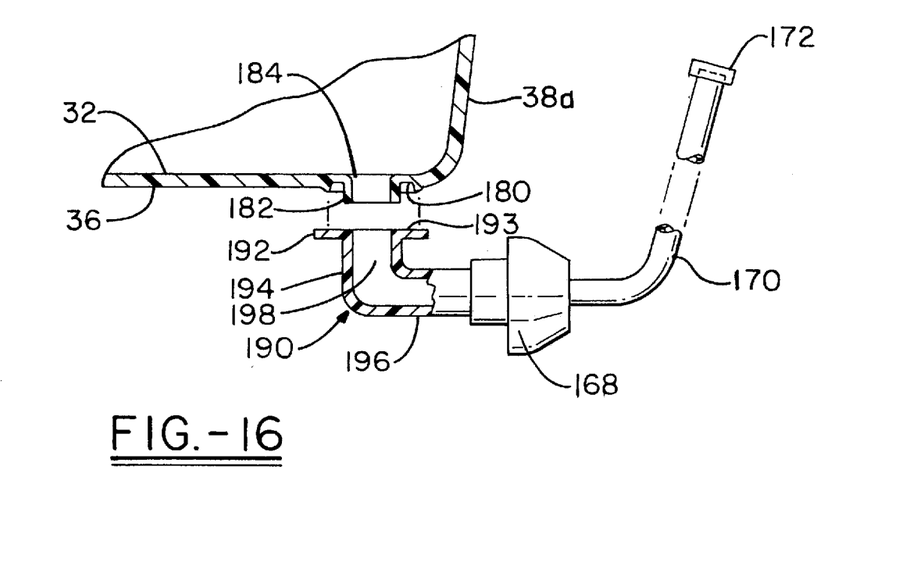
FIG. 16 is an exploded view showing an alternative embodiment of the drain fitting.
Figure 17:
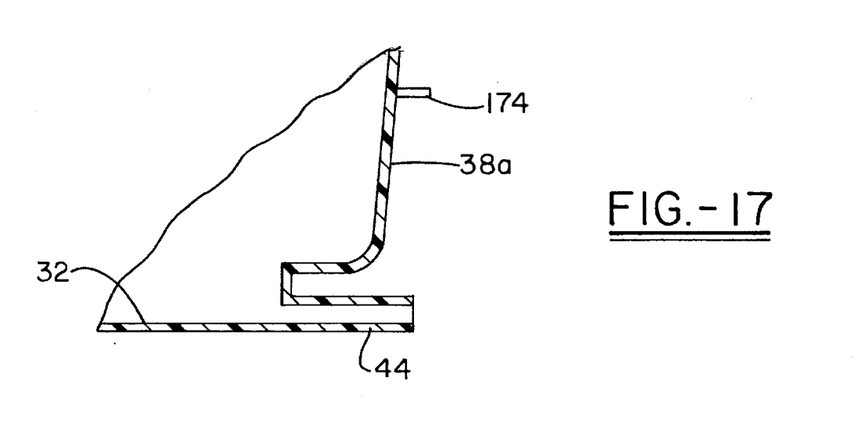
FIG. 17 is a section view of yet another embodiment of the drain spout.

FIGS. 16–17 illustrate alternative embodiments of the drain. An external drain fitting 190 is shown in FIG. 16. The external drain fitting 190 has a generally circular flange 192 having a top surface 193. Extending downwardly from the flange 192 is a neck 194 with an internal bore 198. Substantially perpendicular to the neck 194 is a tubular drain spout 196 which is in fluid connection with the internal bore 198. The spout 196 is sized to permit the attachment of a tube 170, either alone or with an adapter 168.

When the external drain fitting 190 is used, the basin 30 has a generally circular recess 180 on the bottom surface 36 of the floor 32. The recess 180 corresponds in size to the flange 192. Protruding downward from the center of the recess 180 is a neck 182 with an internal bore 184 through the floor 32 of the basin. The neck 182 is sized to fit within the internal bore 198 of the fitting 190. The fitting 190 is attached to the basin floor 32 by a sealing mechanism such as an ultrasonic seal or a glue between the recess 180 and the top surface 193 of the flange 182.

FIG. 17 shows an embodiment of a drain spout 44 which is integral to the floor 32 and sidewall 38a of the basin 30.

As seen in FIGS. 2–4, bottom supports 48 extend downwardly from the bottom surface 36 of the basin floor 32 to enable the basin 30 to stably fit onto a conventional surgical ring stand 22. The bottom supports 48 are positioned and shaped such that they fit within the ring 23 on a surgical ring stand 22, thus providing stability to the basin 30 sitting on the ring stand 22 by restricting lateral movement of the basin 30 relative to the ring stand 22. In the embodiment shown in FIGS. 2–4, there are two bottom supports 48 which are integral to the bottom surface 36 of the floor 32 and which are each,partial circular arcs adapted to securely fit within the ring 23 of the ring stand 22.

Figure 5:
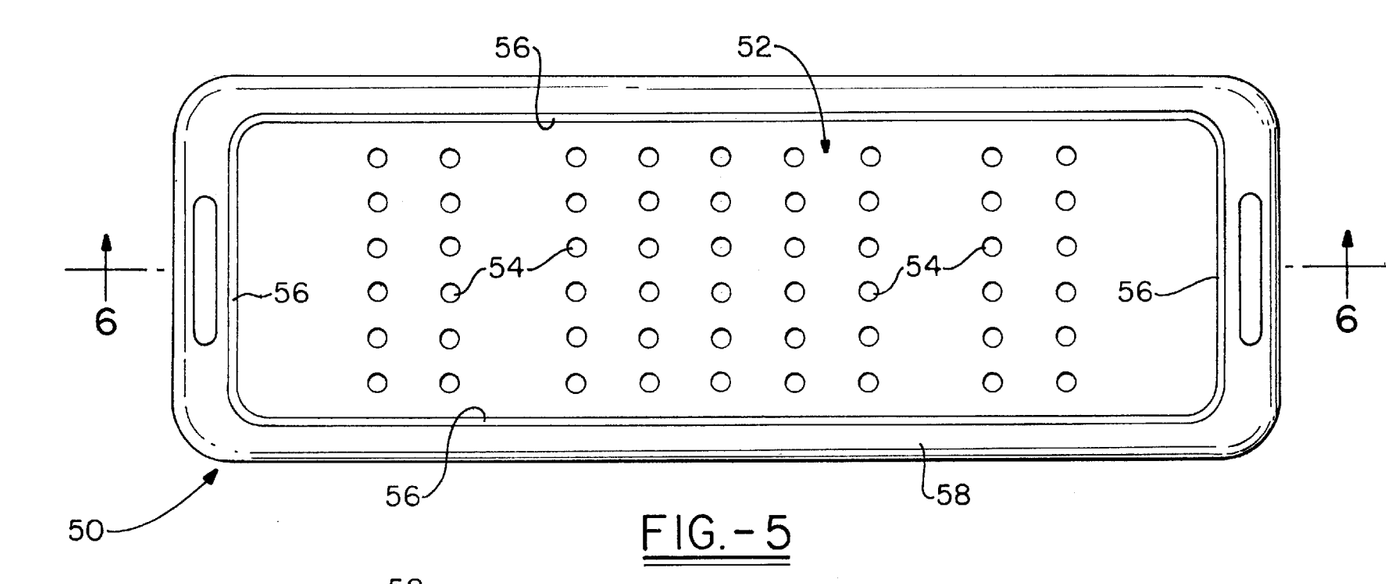
FIG. 5 is a plan view of a rectangular strainer.
Figure 6:
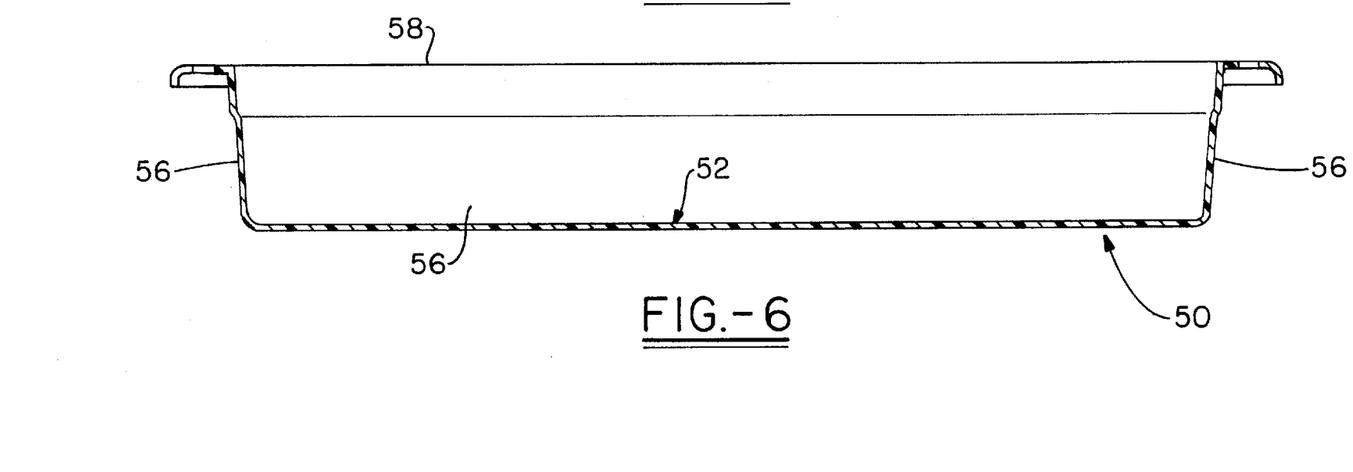
FIG. 6 is a section view of the strainer of FIG. 5 taken along lines 6—6.
Figures 7, 9, 10:
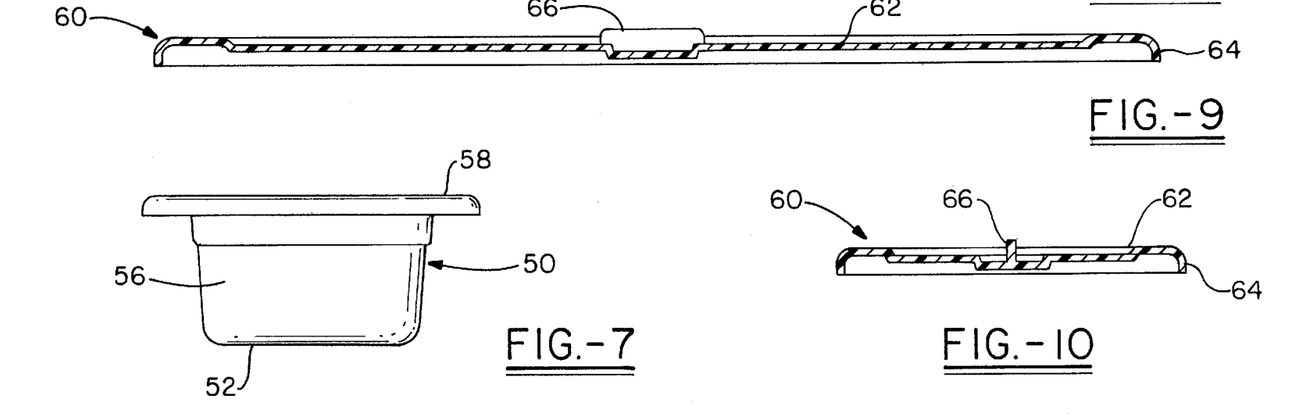
FIG. 7 is an end view of the strainer of FIG. 5.
FIG. 9 is a section view of the cover of FIG. 8 taken along lines 9—9.
FIG. 10 is a section view of the cover of FIG. 8 taken along lines 10—10.

A preferred embodiment of the strainer 50 is shown in greater detail in FIGS. 5–7. The strainer 50 comprises a rectangularly shaped floor 52 with a plurality of holes 54, and four integral side walls 56 extending upwardly from the floor 52 and substantially perpendicular to the floor 52. The size and shape of the strainer 50 corresponds to that of the basin 30 so that the strainer 50 can be nested within the basin 30.

The basin 30 and strainer 50 are large enough to fully contain several surgical instruments of various shapes and sizes that are typically used in modern surgical procedures.

The holes 54 allow solution in the strainer 50 to rapidly drain out into the basin 30 when the strainer 50 is lifted out of the basin 30, thereby exposing any surgical instruments within the basin 30. The number and size of the holes are selected to allow the solution to rapidly drain out without interfering with holding or containing the instruments.

As shown in FIGS. 5–7, the strainer 50 includes a rim 58 integral to the sidewalls 56 and opposite the floor 52. The rim 58 provides a convenient way for lifting the strainer 50 as well as providing additional strength and rigidity.

Figure 8:
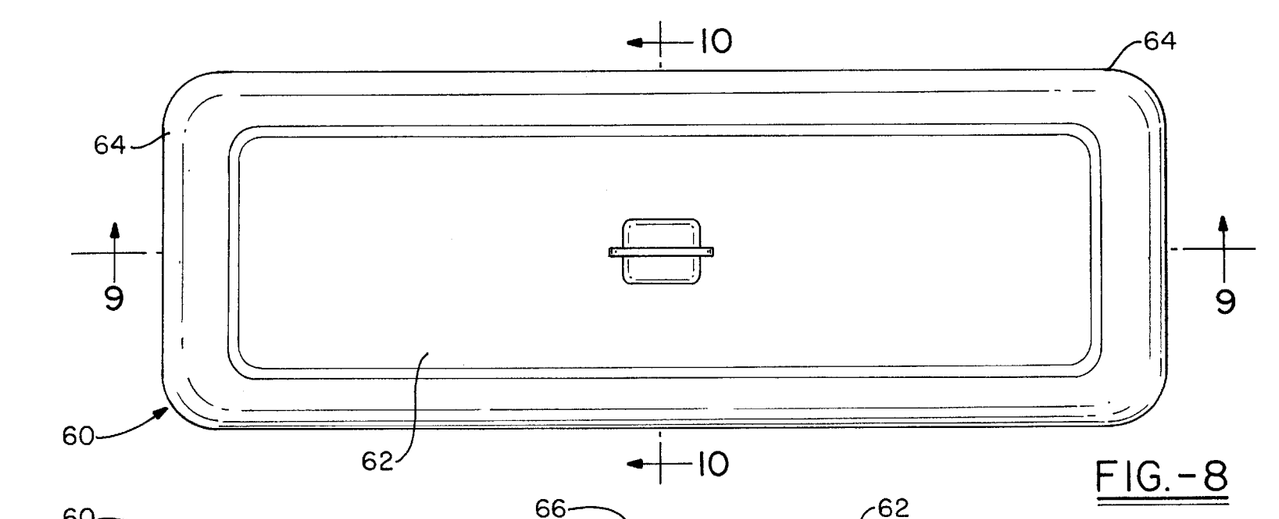
FIG. 8 is a plan view of a cover in an embodiment which includes an integral handle and a rim.

As shown in FIGS. 8–10, the cover 60 has a rectangularly shaped top 62 and an integral rim 64 extending downwardly and substantially perpendicularly to the top 62. The cover 60 includes a handle 66 which is integral to the top 62. The size and shape of the cover 60 correspond to that of the basin 30 and the strainer 50 such that the cover 60 ideally fits over them both. The cover 60 can be either be rigid or flexible. It can also be a shower-cap type cover of the type commonly used in current surgical practice.

Figure 11:
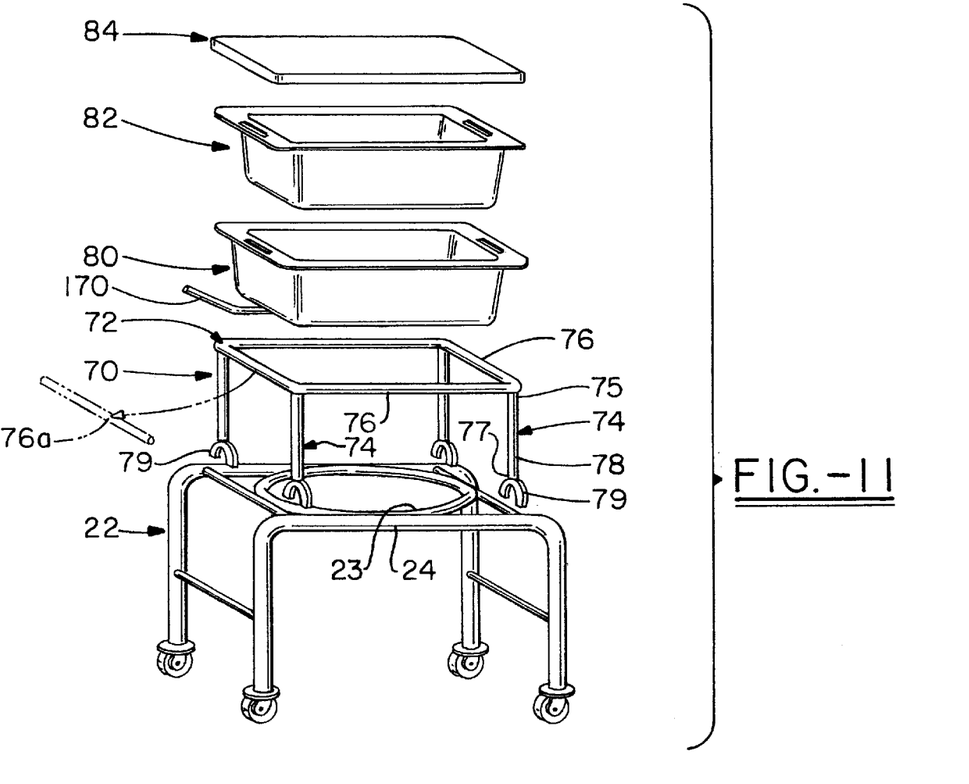
FIG. 11 is an exploded perspective view of an alternative embodiment of the present invention utilizing a conventional surgical ring stand with an adapter for stably holding a rectangular basin that does not have bottom supports.

As shown in FIG. 11, an alternate embodiment has a generally rectangular porous strainer 82, which fits within a rectangular waterproof basin 80. A cover 84 fits onto the assembled basin 80 and strainer 82. An adapter 70 fits onto a conventional surgical ring stand 22 and provides a way for adapting a conventional ring stand 22 for use with the rectangular basin 80. The basin 80 need not include integral bottom supports 48, as in FIG. 1, to fit stably onto the ring stand 22 when the adapter 70 is used.

The adapter 70 shown in FIG. 11 includes a rectangular frame 72 having four cross-members 76 joined together perpendicularly to each other to form the rectangular frame 72. The adapter 70 further includes vertical risers 74 which extend downwardly from the frame 72 and are substantially perpendicular to the frame 72. Each vertical riser 74 includes a leg 78 and a foot 79. The leg 78 is an elongated member having a first end 75 and a second end 77. The first end 75 of the leg 78 is attached to the rectangular frame 72. The foot 79 is attached to the second end 77 of the leg 78 opposite the frame 72. The foot 79 is shaped to fit around a horizontal member 24 on the conventional ring stand 22. In use the adapter 70 is set onto the horizontal members 24 of a ring stand 22 and restricts the lateral movement of the rectangular basin 80 placed onto the ring stand 22 inside the adapter frame 72.

A cross member 76a of the adapter frame 72 can be made to be easily removable, to permit the basin 80 to be slid off of the ring stand 22 without having to lift the basin 80 over the adapter 70 or without having to first remove the adapter 70 from the ring stand 22. Cross member 76a can be made to fit within notches or slots within the adapter frame 72 which would hold the member 76a in place, but would allow the member 76a to be advantageously removed when desired. Alternatively, one end of the cross member 76a can be pivotally attached to the adapter frame 72 to allow the member 76a to swing away from the frame 72 to permit the basin 80 to be slid off the ring stand 22.

Figure 12:
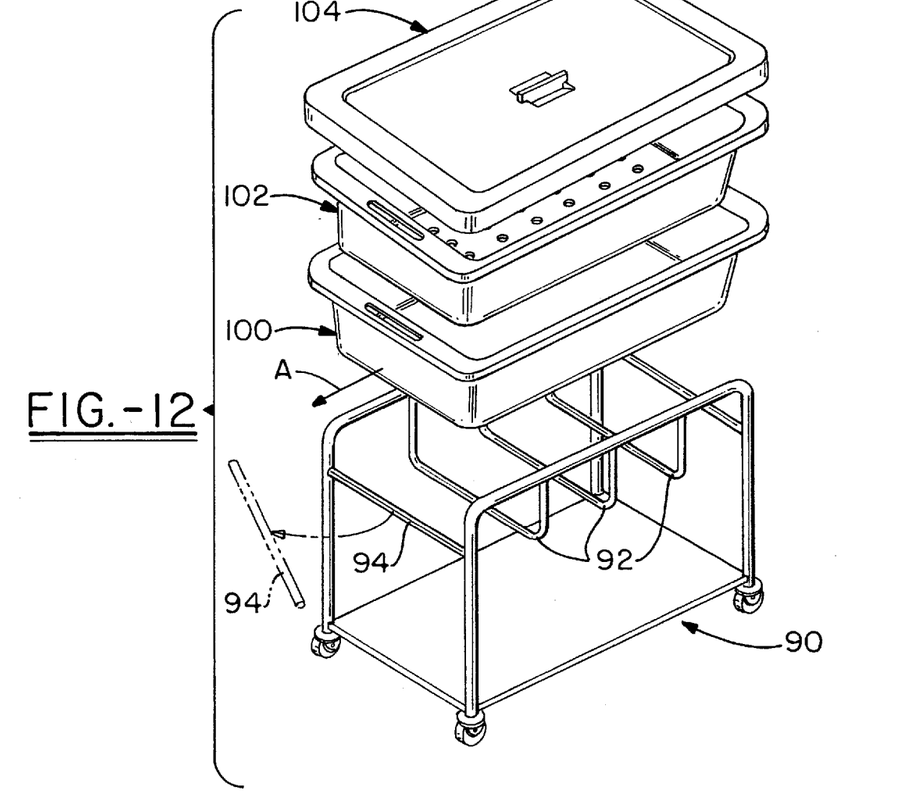

As shown in FIG. 12, yet another alternate embodiment uses a surgical basin stand 90 adapted to stably hold a rectangular basin 100. An adapter 70 is not required. The basin 100 need not have bottom supports 48 to stably support the basin 100. The basin stand includes a plurality of rigid basin supports 92. The basin supports 92 are advantageously shaped and arranged to support the rectangular basin 100 from the bottom surface 36 of the basin 100.

The basin stand 90 may also include a removable restraining member 94. When the restraining member 94 is attached to the basin stand 90, lateral movement of the basin 100 in the direction of arrow A in FIG. 12 with respect to the basin stand 90 is restrained. When the restraining member 94 is removed, the basin 100 may be easily slid off of the basin stand 90 with a minimal amount of lifting required. Restraining member 94 can be made to fit within notches or slots within the basin stand 90 which would hold the member 94 in place, but would allow the member 94 to be advantageously removed when desired. Alternatively, one end of the restraining member 94 can be pivotally attached to the basin stand 90 to allow the member 94 to swing away from the stand 90 to permit the basin 100 to be slid off the basin stand 90. In yet another alternative, the restraining member 94 could be positioned low enough on the basin stand 90 such that the basin 100 will sit stably on the basin stand 90, but can still be slid off of the basin stand 90 when desired without removing the restraining member 94 and without an excessive amount of lifting required.

Figure 13:
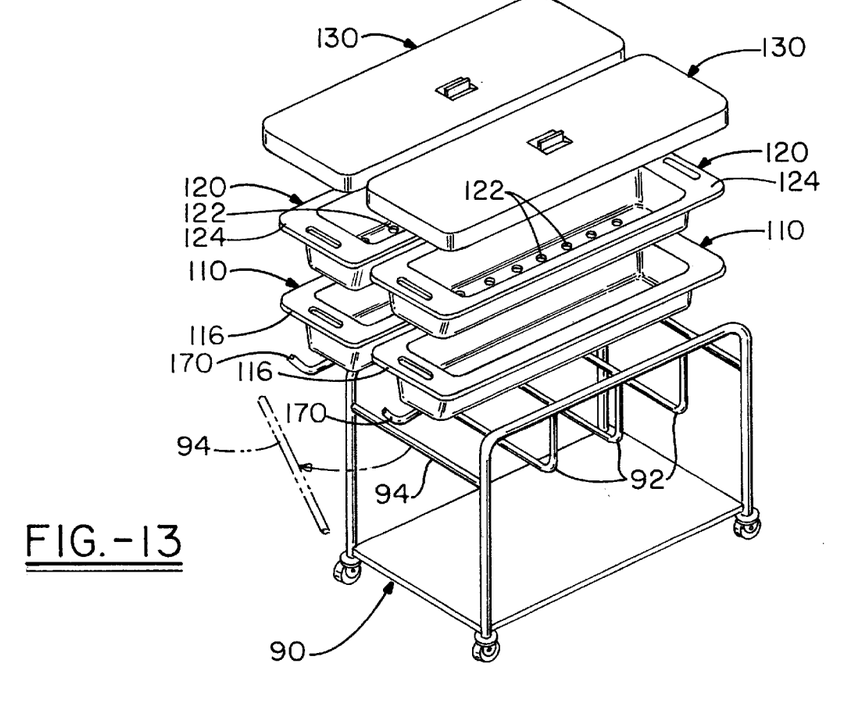
FIG. 13 is an exploded perspective view of yet another embodiment having two narrow basin and strainer combinations which can replace a single wider rectangular basin and strainer.

FIG. 13 shows yet still another embodiment having two narrow rectangular basins 110 in place of a single wide rectangular basin. Each narrow basin 110 includes the same preferred features of the single wide basin, including an integral rim 116 and drain tubes 170. A narrow rectangular strainer 120 nests within each basin 110. Each strainer includes holes 122 and an integral rim 124. Additionally, this embodiment includes two narrow covers 130 which fit onto the assembled strainer and basin combinations.

In the embodiment shown in FIG. 13, the two narrow basins 110 sit adjacent to one another on a surgical basin stand 90 that is adapted to stably hold a single wide rectangular basin. However, the two narrow basins 110 could also be used with a conventional surgical ring stand 22, either alone or with an adapter 70. If the narrow basins 110 are used with a conventional ring stand 22 without an adapter 70, the basins should include bottom supports similar to those shown in FIGS. 1–4.

In addition, although the embodiments depicted herein utilize a single ring stand 22, it is anticipated that a double ring stand could also be utilized, either with an adapter similar to the adapter 70 shown, or with a basin with bottom supports similar to those shown in FIGS. 1–4. Yet another rigid support that could be used with the present system is a stainless steel table which typically would be draped with sterile covers before use.

Thus, while several embodiments have been shown and described, various other modifications may be made without departing from the spirit and scope of the invention.

We claim:

1. A system for handling surgical tools and instruments comprising:

a waterproof and generally rectangular basin including a floor having a top surface and a bottom surface with at least one bottom support extending outwardly from the bottom surface of the floor;

a surgical ring stand containing at least one ring; and the at least one bottom support having a curvature generally matching the curvature of the at least one ring on the ringstand.

2. The system of claim 1 further comprising a generally rectangular strainer sized to fit within the basin.

3. The system of claim 1, wherein the basin has a drain through the floor.

4. The system of claim 1, further comprising a cover sized to fully close the basin.

5. A system for handling surgical tools and instruments comprising:

(a) a generally rectangular strainer;

(b) a waterproof rectangular basin sized to receive the strainer, wherein the basin comprises a rectangular floor and a plurality of sidewalls which extend upwardly from the floor; and (c) an adapter comprising a rectangular frame sized to receive the basin and a plurality of vertical risers attached to the frame and extending downward from the frame, the vertical risers each having a foot portion attached at a lower end of the vertical riser which can engage a horizontal member of a conventional surgical ring stand.

6. The system of claim 5, further comprising a cover sized to fully close the assembled basin and strainer.

7. A kit comprising the components of the system of claim 5, contained within a sealed, storable, package as a prepackaged kit enabling convenient deployment and use of the system of claim 5 and convenient storage of the components prior to such use.

8. A method of handling contaminated surgical instruments comprising the steps of:

(a) placing an adapter onto a conventional surgical ring stand having at least one ring;

(b) placing a generally rectangular basin within the adapter and onto the ring stand;

(c) partially filling the basin with a sterile solution;

(d) placing surgical instruments into the solution after the instruments are used in surgery.

9. The method of claim 8, further comprising the step of placing a generally rectangular strainer into the basin before partially filling the basin with the sterile solution.

10. The method of claim 9, further comprising the step of lifting the strainer out of the basin after the surgical instruments have been placed into the solution, allowing the solution to drain into the basin and thereby exposing the instruments in the strainer.

11. The method of claim 9 wherein the strainer is placed into the basin after partially filling the basin with the solution.

12. The method of claim 8, further comprising the step of placing a cover onto the basin after placing the surgical instruments into the basin.

13. The system of claim 1 wherein the basin has two bottom supports.

14. The system of claim 5 further comprising a displaceable cross member at one end of the frame of the adapter.

* * * * *